(12) United States Patent
Meyer et al.

(10) Patent No.: US 6,340,745 B1
(45) Date of Patent: Jan. 22, 2002

(54) PHTHALOCYANINE AND USE OF PHTHALOCYANINE AS A MARKING AGENT

(75) Inventors: Frank Meyer, Mannheim; Christos Vamvakaris, Kallstadt; Karin Heidrun Beck, Ludwigshafen; Gerhard Wagenblast; Bernhard Albert, both of Wachenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,653

(22) PCT Filed: May 13, 1998

(86) PCT No.: PCT/EP98/02824

§ 371 Date: Nov. 19, 1999

§ 102(e) Date: Nov. 19, 1999

(87) PCT Pub. No.: WO98/52950

PCT Pub. Date: Nov. 26, 1998

(30) Foreign Application Priority Data

May 22, 1997 (DE) .......................... 197 21 399

(51) Int. Cl.[7] ...................... C07D 487/22; C09B 47/04; C09B 67/12
(52) U.S. Cl. ...................... 534/702; 534/707; 534/708; 534/726; 540/123; 540/124; 540/125; 540/127; 540/128; 540/140; 208/14; 208/370
(58) Field of Search .................. 540/123, 124, 540/125, 127, 128, 140; 534/702, 707, 708, 726; 208/14, 370

(56) References Cited

FOREIGN PATENT DOCUMENTS

| EP | 0 190 444 | * | 4/1996 |
| WO | WO 94/02570 | | 2/1994 |
| WO | 96/10620 | * | 4/1996 |

OTHER PUBLICATIONS

F.A. Moser, et al., The Phthalocyanines, vol. II, Manufacture and Applications, Table of Contents, 20 pages, 1983.
B.L. Wheeler, et al., J. Am. Chem. Soc., vol. 106, pp. 7404–7410, "A Silicon Phthalocyanine and a Silicon Naphthalocyanine: Synthesis, Electrochemistry, and Electrogenerated Chemiluminescence", 1984.

* cited by examiner

Primary Examiner—T. A. Solola
(74) Attorney, Agent, or Firm—Oblon, Spivak, McClelland, Maier & Neustadt, P.C.

(57) ABSTRACT

Phthalocyanines of the formula where

Me is twice hydrogen, twice lithium, magnesium, zinc, copper, nickel, VO, TiO, AlCl, AlOH, AlOCOCH$_3$, AlOCOCF$_3$, SiCl$_2$ or Si(OH)$_2$, at least four of the radicals $R^1$ to $R^{16}$ are each independently of the others a five- or six-membered saturated nitrogen-containing heterocyclic radical which is bonded to the phthalocyanine structure via a ring nitrogen atom and which can additionally contain further hetero atoms, and any remaining radicals $R^1$ to $R^{16}$ are each hydrogen, halogen, hydroxysulfonyl or $C_1$–$C_4$-dialkylsulfamoyl, subject to the proviso that tetrakispiperidinylphthalocyanine shall be excluded, and heterocyclyl-substituted phthalocyanines are useful for marking liquids, in particular mineral oils.

11 Claims, No Drawings

PHTHALOCYANINE AND USE OF PHTHALOCYANINE AS A MARKING AGENT

This application is a 371 of PCT/EP98/02824 filed May 13, 1998.

The present invention relates to novel phthalocyanines of the formula I

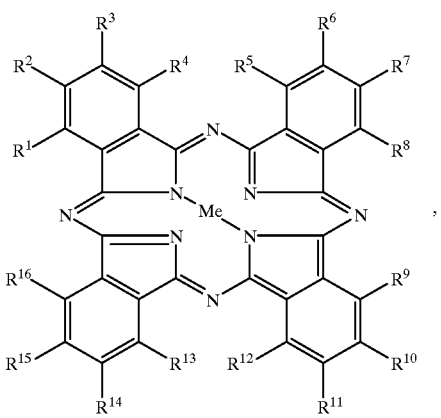

(I)

where

Me is twice hydrogen, twice lithium, magnesium, zinc, copper, nickel, VO, TiO, AlCl, AlOH, AlOCOCH$_3$, AlOCOCF$_3$, SiCl$_2$ or Si(OH)$_2$, at least four of the radicals $R^1$ to $R^{16}$ are each independently of the others a five- or six-membered saturated nitrogen-containing heterocyclic radical which is bonded to the phthalocyanine structure via a ring nitrogen atom and which can additionally contain one or two further nitrogen atoms or a further oxygen or sulfur atom, and any remaining radicals $R^1$ to $R^{16}$ are each hydrogen, halogen, hydroxysulfonyl or $C_1$–$C_4$-dialkylsulfamoyl, subject to the proviso that tetrakispiperidinylphthalocyanine shall be excluded, to the use of heterocyclyl-substituted phthalocyanines for marking liquids, and to mineral oils comprising such phthalocyanines.

J. Gen. Chem. USSR, 51 (1981), 1405–1411, discloses the preparation of tetrakispiperidinylphthalocyanine. WO-A-94/02570 and WO-A-96/10620 describe phthalocyanines as markers for liquids, especially mineral oils.

However, it has been found that the markers described therein still have defects in their application properties, especially insufficient solubility and insufficient chemical stability in solution.

It is an object of the present invention to provide suitable phthalocyanines having an improved property profile.

We have found that this object is achieved by the phthalocyanines of the formula I more particularly defined at the beginning.

Any alkyl appearing in the formulae mentioned herein may be straight-chain or branched.

Halogen is for example fluorine, chlorine, bromine or iodine.

$C_1$–$C_4$-Dialkylsulfamoyl is for example dimethylsulfamoyl, diethylsulfamoyl, dipropylsulfamoyl, diisopropylsulfamoyl, dibutylsulfamoyl or N-methyl-N-ethylsulfamoyl.

Suitable five- or six-membered saturated nitrogen-containing heterocyclic radicals which are attached to the phthalocyanine structure via a ring nitrogen atom and can additionally contain one or two further nitrogen atoms or a further oxygen or sulfur atom in the ring are derived for example from pyrrolidine, pyrazolidine, imidazolidine, oxazolidine, isoxazolidine, piperidine, piperazine, morpholine or thiomorpholine as basic structure.

The heterocyclic radicals can be monosubstituted or polysubstituted, preferably monosubstituted, disubstituted or trisubstituted, especially monosubstituted. Preferred substituents are $C_1$–$C_4$-alkyl, benzyl, phenylethyl or phenyl.

Suitable heterocyclic radicals are for example pyrrolidin-1-yl, 2- or 3-methylpyrrolidin-1-yl, 2,4-dimethyl-3-ethylpyrrolidinyl, pyrazolidin-1-yl, 2-, 3-, 4- or 5-methylpyrazolidin-1-yl, imidazolidin-1-yl, 2-, 3-, 4- or 5-methylimidazolidin-1-yl, oxazolidin-3-yl, 2-, 4- or 5-methyloxazolidin-3-yl, isoxazolidin-2-yl, 3-, 4- or 5-methylisoxazolidin-2-yl, piperidin-1-yl, 2-, 3-, 4-methyl-, -ethyl- or -benzyl-piperidin-1-yl, 2,6-dimethylpiperidin-1-yl, piperazin-1-yl, 4-($C_1$–$C_4$-alkyl)piperazin-1-yl, such as 4-methyl- or 4-ethylpiperazin-1-yl, morpholin-4-yl, thiomorpholin-4-yl or thiomorpholin-4-yl S,S-dioxide.

Preferred heterocyclic radicals are derived from pyrrolidine, piperidine, piperazine or morpholine as basic structure.

Preference is given to phthalocyanines of the formula I wherein four of the radicals $R^1$ to $R^{16}$ are each a heterocyclic radical.

Preference is further given to phthalocyanines of the formula I wherein four of the radicals $R^1$ to $R^{16}$ are each a heterocyclic radical and the remaining radicals $R^1$ to $R^{16}$ are each hydrogen.

Preference is further given to phthalocyanines of the formula I which have heterocyclic radicals which are monosubstituted or polysubstituted, preferably monosubstituted, disubstituted or trisubstituted, especially monosubstituted, by $C_1$–$C_4$-alkyl, benzyl, phenylethyl or phenyl.

Preference is given to phthalocyanines which conform to the formula Ia or Ib

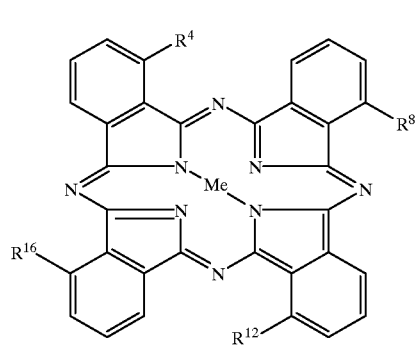

(Ia)

-continued

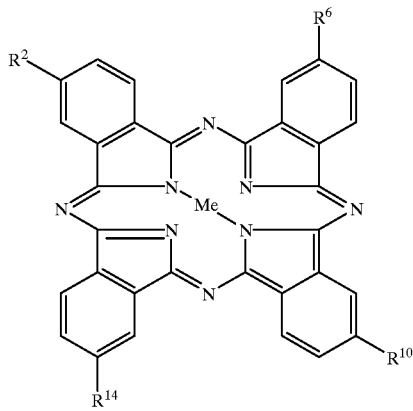

(Ib)

where
the radicals $R^4$, $R^8$, $R^{12}$ and $R^{16}$ and also $R^2$, $R^6$, $R^{10}$ and $R^{14}$ are each a heterocyclic radical and Me is in each case as defined above, and also their positional isomers in relation to the radicals $R^4$, $R^8$, $R^{12}$ and $R^{16}$ and also $R^2$, $R^6$, $R^{10}$ and $R^{14}$.

Of particular interest are phthalocyanines of the formula Ia or Ib, where $R^4$, $R^8$, $R^{12}$ and $R^{16}$ and also $R^2$, $R^6$, $R^{10}$ and $R^{14}$ are each pyrrolidin-1-yl, piperidin-1-yl, piperazin-1-yl or morpholin-4-yl, which radicals can be monosubstituted, disubstituted or trisubstituted, preferably monosubstituted, by $C_1$–$C_4$-alkyl, benzyl, phenylethyl or phenyl.

Preference is also given to phthalocyanines of the formula I in which the substituents are selected from a combination of the above-recited preferred substituents.

The novel phthalocyanines of the formula I are obtainable in a conventional manner, for example as described in J. Gen. Chem. USSR 51 (1981) 1405–1411, F. H. Moser, A. L. Thomas, The Phthalocyanines, CRC Press, Boca Rota, Fla., 1983, or J. Am. Chem. Soc. 106 (1984) 7404–7410. For instance, phthalonitriles which, in conformance with the formula I, bear suitable substituents can be made to react in an inert diluent in the presence of a base, optionally in the presence of a metallizing reagent.

The present invention further provides for the use of phthalocyanines of the formula II

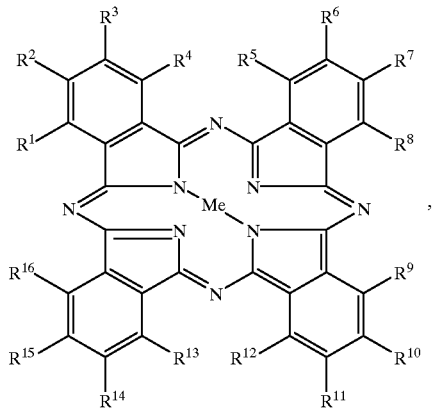

(II)

where
Me is twice hydrogen, twice lithium, magnesium, zinc, copper, nickel, VO, TiO, AlCl, AlOH, $AlOCOCH_3$, $AlOCOCF_3$, $SiCl_2$ or $Si(OH)_2$, at least four of the radicals $R^1$ to $R^{16}$ are each independently of the others a five- or six-membered saturated nitrogen-containing heterocyclic radical which is bonded to the phthalocyanine structure via a ring nitrogen atom and which can additionally contain one or two further nitrogen atoms or a further oxygen or sulfur atom, and any remaining radicals $R^1$ to $R^{16}$ are each hydrogen, halogen, hydroxysulfonyl or $C_1$–$C_4$-dialkylsulfamoyl, as markers for liquids.

Preference is given to the use of phthalocyanines of the formula I wherein four of the radicals $R^1$ to $R^{16}$ are each a heterocyclic radical.

Preference is further given to the use of phthalocyanines of the formula I wherein four of the radicals $R^1$ to $R^{16}$ are each a heterocyclic radical and the remaining radicals $R^1$ to $R^{16}$ are each hydrogen.

Preference is further given to the use of phthalocyanines of the formula I which have heterocyclic radicals which are monosubstituted or polysubstituted, preferably monosubstituted, disubstituted or trisubstituted, especially monosubstituted, by $C_1$–$C_4$-alkyl, benzyl, phenylethyl or phenyl.

Particular preference is given to the use of phthalocyanines which conform to the formula Ia or Ib

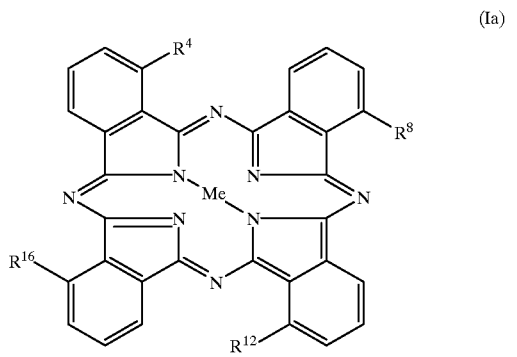

(Ia)

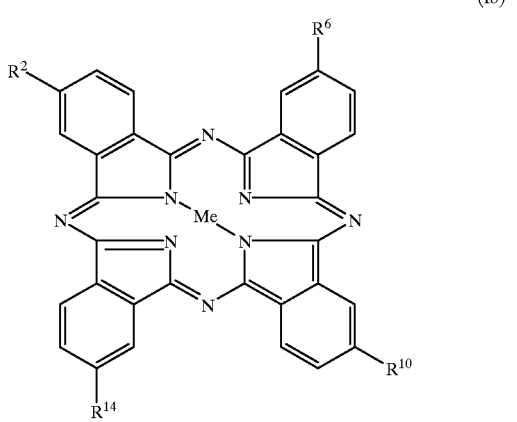

(Ib)

where
the radicals $R^4$, $R^8$, $R^{12}$ and $R^{16}$ and also $R^2$, $R^6$, $R^{10}$ and $R^{14}$ are each a heterocyclic radical and Me is in each case as defined above, and also their positional isomers in relation to the radicals $R^4$, $R^8$, $R^{12}$ and $R^{16}$ and also $R^2$, $R^6$, $R^{10}$ and $R^{14}$.

Of particular interest is the use of phthalocyanines of the formula Ia or Ib, where $R^4$, $R^8$, $R^{12}$ and $R^{16}$ and also $R^2$, $R^6$, $R^{10}$ and $R^{14}$ are each pyrrolidin-1-yl, piperidin-1-yl, piperazin-1-yl or morpholin-4-yl, which radicals can be monosubstituted, disubstituted or trisubstituted, preferably monosubstituted, by $C_1$–$C_4$-alkyl, benzyl, phenylethyl or phenyl.

It is frequently necessary to mark liquids in order that the liquids thus marked may be detected later, for example in use, by means of suitable methods.

In this way it is possible, for example, to distinguish fuel oil and diesel oil.

Suitable solvents for marking according to the invention by means of the compounds more particularly defined above are especially organic liquids, for example alcohols, such as methanol, ethanol, propanol, isopropanol, butanol, isobutanol, sec-butanol, pentanol, isopentanol, neopentanol or hexanol, glycols, such as 1,2-ethylene glycol, 1,2- or 1,3-propylene glycol, 1,2-, 2,3- or 1,4-butylene glycol, di- or triethylene glycol or di- or tripropylene glycol, ethers, such as methyl tert-butyl ether, 1,2-ethylene glycol monomethyl or dimethyl ether, 1,2-ethylene glycol monoethyl or diethyl ether, 3-methoxypropanol, 3-isopropoxypropanol, tetrahydrofuran or dioxane, ketones, such as acetone, methyl ethyl ketone or diacetone alcohol, esters, such as methyl acetate, ethyl acetate, propyl acetate or butyl acetate, aliphatic or aromatic hydrocarbons such as pentane, hexane, heptane, octane, isooctane, petroleum ether, toluene, xylene, ethylbenzene, tetralin, decalin, dimethylnaphthalene, mineral spirit, mineral oils, such as gasoline, kerosene, diesel oil or fuel oil, natural oils, such as olive oil, soybean oil or sunflower oil, or natural or synthetic engine, hydraulic or gear oils, for example vehicle engine oil or sewing machine oil, or brake fluids.

The abovementioned compounds are particularly useful for marking mineral oils where some form of identification is mandatory, for example for tax reasons. To keep the costs for this to a minimum, it is usually desirable to use very high yield dyes for the coloring. However, even so-called strong dyes are no longer detectable purely visually in high dilution in mineral oils.

Based on the weight of the liquid to be marked, from 1 to 1000 ppb, preferably from 1 to 500 ppb, especially from 100 ppb to 500 ppb, of phthalocyanine II are used.

To mark the liquids, especially mineral oils, the phthalocyanines of the formula II are generally employed in the form of solutions. Suitable solvents are preferably aromatic hydrocarbons, such as $C_1$–$C_{20}$-alkyl-substituted aromatic hydrocarbons, for example toluene, xylene or Shellsol® (from Shell). To avoid the resulting solutions having an excessively high viscosity, the concentration of phthalocyanine II is generally chosen within the range from 0.5 to 60% by weight, based on the solution.

The present invention further provides mineral oils comprising one or more phthalocyanines of the formula II.

The phthalocyanines II generally have their absorption maximum within the range from 600 to 1200 nm and/or fluoresce within the range from 620 to 1200 nm and are thus easy to detect using suitable instruments.

The detection of the phthalocyanines II can be effected in a conventional manner, for example by measuring the IR absorption spectrum of the liquids to be examined.

However, it is also possible to excite the fluorescence of the phthalocyanines II present in the liquids, advantageously using a semiconductor laser or a semiconductor diode. It is particularly advantageous to employ a semiconductor laser or diode having a maximum emission wavelength within the spectral region from $\lambda_{max}$ −100 nm to $\lambda_{max}$ +20 nm. Here λmax is the wavelength of the absorption maximum of the marker. The maximum emission wavelength is within the range from 620 to 1200 nm.

The fluorescence light thus generated is advantageously detected using a semiconductor detector, especially with a silicon photodiode or a germanium photodiode.

Detection is accomplished particularly advantageously when the detector is disposed behind an interference filter and/or a cutoff filter (having a short wave transmission cutoff within the range from $\lambda_{max}$ to $\lambda_{max}$ +80 nm) and/or a polarizer.

By means of the abovementioned compounds, it is very simple to detect marked liquids, even if the phthalocyanines II are present only in a concentration of about 1 ppm (detection by absorption) or about 5 ppb (detection by fluorescence).

The phthalocyanines of the formula II are highly soluble in the liquids to be marked. They also have high chemical stability in solution.

The Examples which follow illustrate the invention.

A) Preparation

EXAMPLE 1

56.3 g (0.325 mol) of 30% strength by weight methanolic sodium methoxide solution were dissolved in 1 l of n-butanol and excess methanol was distilled off until a constant boiling point of 117° C. was attained. 112.5 g of 3-(3'-methylpiperidin-1-yl)phthalonitrile were then added, and the mixture was stirred under reflux for 6 h. It was then added to 1.5 l of methanol, and the mixture was subsequently stirred for 1 h and filtered with suction. The residue was washed in succession with methanol, water and acetone and then air dried.

This gave 101.4 g of phthalocyanine of the formula

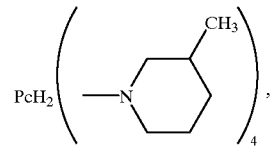

where $PcH_2$ is the quadrivalent radical of phthalocyanine whose central unit is twice hydrogen.

The same method gives the phthalocyanines recited below in Table 1.

TABLE 1

| | PcMe(R)$_4$ | |
|---|---|---|
| Ex. No. | Me | R |
| 2 | 2H | CH$_3$-piperidinyl |
| 3 | 2H | 4-CH$_3$-piperidinyl |
| 4 | 2H | 4-CH$_2$C$_6$H$_5$-piperidinyl |
| 5 | 2H | morpholinyl |

TABLE 1-continued

| Ex. No. | PcMe(R)₄ Me | R |
|---|---|---|
| 6 | 2H | 1-methyl-1,3-dihydro-2H-benzimidazol-2-one |
| 7 | 2H | 8-methyl-1,4-dioxa-8-azaspiro[4.5]decane |
| 8 | 2H | 2-ethyl-1-methylpiperidine |
| 9 | 2H | N,N-diethyl-1-methylpiperidine-3-carboxamide |
| 10 | 2H | 1,3,3-trimethylpiperidine |
| 11 | 2H | 1,3,5-trimethylpiperidine |
| 12 | 2H | 1-methyl-4-phenylpiperidine |
| 13 | 2H | 1-methyl-2-(pyridin-4-yl)piperidine |
| 14 | 2H | 1'-methyl-1,4'-bipiperidine |
| 15 | 2H | 2-methyldecahydroisoquinoline |
| 16 | 2H | 5-ethyl-1,2-dimethylpiperidine |
| 17 | 2H | 2-[(dimethylamino)methyl]-1-methylpiperidine |
| 18 | 2H | N,N,1-trimethylpiperidin-4-amine |
| 19 | 2H | 1-methyl-4-propylpiperidine |
| 20 | 2H | 1-methyl-4-(3-phenylpropyl)piperidine |
| 21 | AlCl | 1,3-dimethylpiperidine |
| 22 | AlCl | 2-ethyl-1-methylpiperidine |
| 23 | AlCl | 1,2-dimethylpiperidine |
| 24 | AlCl | 4-benzyl-1-methylpiperidine |
| 25 | AlCl | 1-methyl-4-phenylpiperidine |
| 26 | SiCl₂ | 1,3-dimethylpiperidine |
| 27 | SiCl₂ | 1,2-dimethylpiperidine |

TABLE 1-continued

PcMe(R)₄

| Ex. No. | Me | R |
|---|---|---|
| 28 | AlOCOCF₃ | 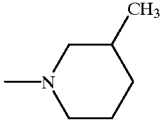 |
| 29 | AlOH | 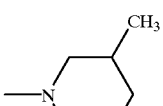 |
| 30 | 2H | 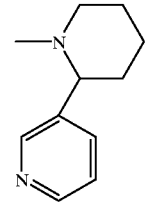 |
| 31 | 2H | 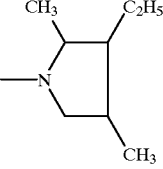 |
| 32 | 2H | 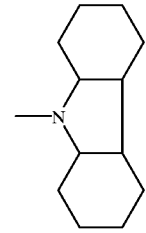 |
| 33 | AlCl | 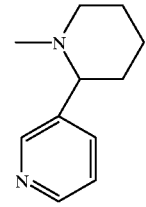 |
| 34 | AlCl | 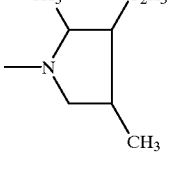 |
| 35 | AlCl | 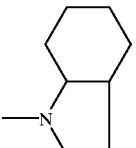 |
| 36 | AlOCOCF₃ | 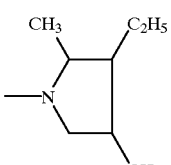 |
| 37 | SiCl₂ | 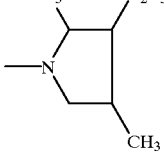 |

B) Application

I. Detection by Absorption in IR Region

Sufficient dye of the formula

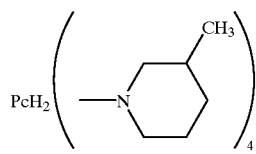

was dissolved in one of the liquids mentioned in Table 2 to obtain a solution having a dye content of 10 ppm. The absorption of these solutions in the IR region was measured in each case by means of a commercially available spectrometer (1 cm cell).

TABLE 2

| Dye content [ppm] | Absorption | Absorption maximum [nm] |
|---|---|---|
| Diesel motor fuel | 1.10 | 762 |
| Unleaded gasoline | 1.10 | 760 |
| Ethanol | 1.05 | 771 |
| Toluene | 1.15 | 770 |

To measure the stability of the dye in storage, the samples were stored for several weeks at room temperature (RT) and at 50° C., and the absorption was measured using a commercially available spectrometer. Specifically, the results obtained were as follows:

TABLE 3

| Test duration (temp.) | Ethanol | Toluene | Diesel motor fuel | Unleaded gasoline |
|---|---|---|---|---|
| 0 time (RT) | 1.0535 | 1.1486 | 1.0964 | 1.0993 |
| 1 week (RT) | 1.0601 | 1.152 | 1.0977 | 1.0937 |
| 2 weeks (RT) | 1.0479 | 1.1484 | 1.097 | 1.1014 |
| 4 weeks (RT) | 1.0467 | 1.1517 | 1.097 | 1.098 |
| 8 Weeks (RT) | 1.0181 | 1.1443 | 1.078 | 1.0869 |
| 1 week (50° C.) | 1.0467 | 1.1421 | 1.016 | 1.0926 |
| 2 weeks (50° C.) | 1.0521 | 1.1538 | 1.0917 | 1.0989 |
| 4 weeks (50° C.) | 1.043 | 1.1438 | 1.0937 | 1.0864 |
| 8 weeks (50° C.) | 1.0467 | 1.1445 | 1.0455 | 1.0617 |

II. Detection by Fluorescence in NIR Region

The marker fluorescence is excited using the emission of a commercial semiconductor diode laser. The parallel laser beam is directed at the sample in a 1 cm cell. To double the excitation intensity, the transmitted light beam is reflected by a mirror and passed once more through the sample.

The fluorescence light is imaged by means of optical elements (lens system) on the detector, a silicon photodiode. The light emitted to the rear is likewise directed onto the silicon photodiode by a concave mirror.

Interfering light (scattered excitation light) is removed from the fluorescence light using cutoff and/or interference filters and/or a polarizer (NIR polarization film).

The polarizer is optimized so that the direction of the maximum transmission is perpendicular to the plane of polarization of the excitation light.

Sufficient dye of the formula

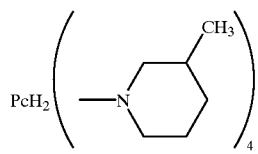

was dissolved in diesel motor fuel to obtain a solution having a dye content of 250 ppb.

This solution was measured by general method II using the following apparatus parameters:

excitation: semiconductor diode laser of laser wavelength 789 nm; CW power 2 mW (modulation: 1.9 kHz)

Filter: long-pass interference filter 805 nm.

Photodetector: silicon PIN diode of 1 cm² area. The photocurrent was detected using a lock-in amplifier. The essential aspect of these measurements was the stability of the dye in storage at room temperature. The measurements obtained are recited in Table 3.

TABLE 3

| Time [weeks] | Absorbance at $\lambda_{max}$ [nm] | Fluorescence signal (in scale divisions) |
|---|---|---|
| 0 | 789 | 1.96 |
| 1 | 789 | 1.98 |
| 2 | 789 | 2.04 |
| 3 | 789 | 1.90 |
| 4 | 789 | 1.95 |

We claim:
1. A phthalocyanine of formula I' or I"

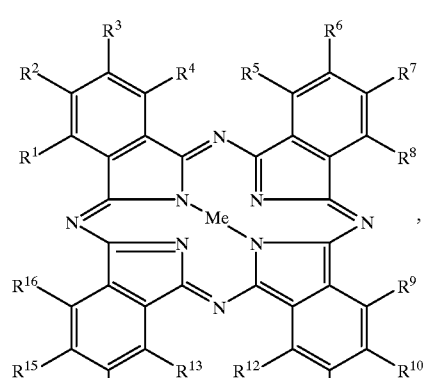

wherein:

in formula I', Me is magnesium, zinc, copper, nickel, VO, TiO, AlCl, AlOH, AlOCOCH$_3$, AlOCOCF$_3$, SiCl$_2$ or Si(OH)$_2$, and wherein in formula I", both Y groups are hydrogen ion or lithium ion, and at least four of the radicals $R^1$ to $R^{16}$ in each of formulas I' and I" are each independently of the others a nitrogen-containing heterocyclic radical which is monosubstituted or polysubstituted by $C_1$–$C_4$-alkyl, benzyl, phenylethyl or phenyl and is bonded to the phthalocyanine structure via a ring nitrogen atom of the heterocyclic radical which is a member selected from the group consisting of pyrrolidinyl, pyrazolidinyl, imidazolidinyl, oxazolidinyl, isoxazolidinyl, piperidinyl, piperazinyl, morpholinyl and thiomorpholinyl, and any remaining radicals $R^1$ and $R^{16}$ are each hydrogen, halogen, hydroxysulfonyl of $C_1$–$C_4$-dialkylsulfamoyl.

2. Phthalocyanines as claimed in claim 1, wherein four of the radicals $R^1$ to $R^{16}$ are each a heterocyclic radical.

3. The phthalocyanine as claimed in claim 1, wherein four of the radicals $R^1$ to $R^{16}$ are each a heterocyclic radical and the remaining radicals $R^1$ to $R^{16}$ are each hydrogen.

4. The phthalocyanine as claimed in claim 1, wherein formula I' conforms to the formula Ia or Ib:

(Ia)

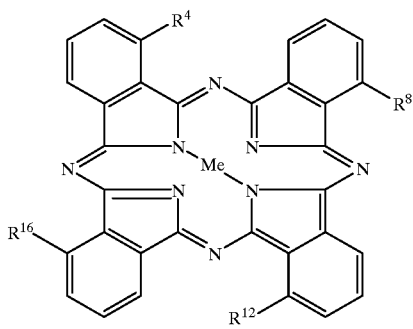

(Ib)

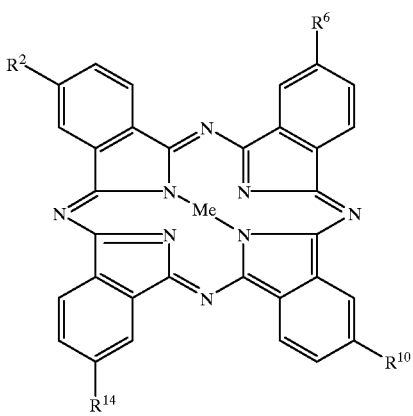

where the radicals $R^4$, $R^8$, $R^{12}$ and $R^{16}$ and $R^2$, $R^6$, $R^{10}$ and $R^{14}$ are each a heterocyclic radical and Me is in each case as defined above, and their positional isomers in relation to the radicals $R^4$, $R^8$, $R^{12}$ and $R^{16}$ and also $R^2$, $R^6$, $R^{10}$ and $R^{14}$.

5. The phthalocyanine of claim 1, wherein said heterocyclic radical is a member selected from the group consisting of:

pyrrolidin-1-yl; 2- or 3-methylpyrrolidin-1-yl; 2,4-dimethyl-3-ethylpyrrolidinyl; pyrazolidin-1-yl; 2,-, 3-, 4- or 5-methylpyrazolidin-1-yl; imidazolidin-1-yl; 2-, 3-, 4- or 5-methylimidazolidin-1-yl; oxaolidin-3-yl; 2-, 4- or 5-methyloxazolidin-3-yl; isoxazolidin-2-yl, 3-, 4- or 5-methylisoxazolidin-2-yl, piperidin-1-yl, 2-, 3-, 4-methyl-, ethyl- or -benzyl-piperidin-1-yl, 2,6-dimethylpiperidin-1-yl, piperazin-1-yl, 4-($C_1$–$C_4$-alkyl)piperazin-1-yl, morpholin-4-yl, thiomorpholin-4-yl or thiomorpholin-4-yl S,S-dioxide.

6. The phthalocyanine according to claim 1, wherein said $C_1$–$C_4$-dialkylsulfamoyl is dimethylsulfamoyl, diethylsulfamoyl, dipropylsulfamoyl, diisopropylsulfamoyl, dibutylsulfamoyl or N-methyl-N-ethylsulfamoyl.

7. A phthalocyanine of formula I' or I''

(I')

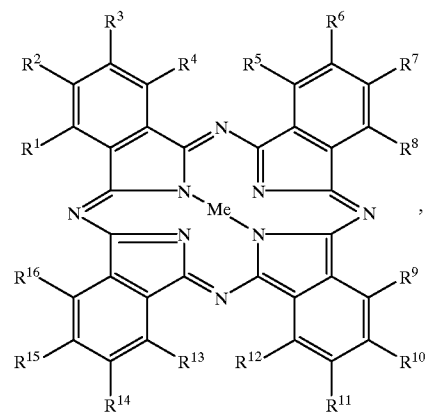

or (I'')

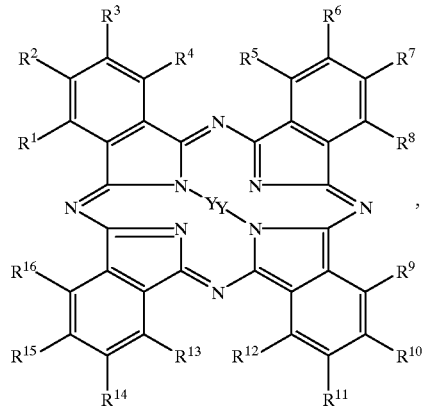

wherein:

in formula I', Me is zinc, AlCl, AlOH, AlOCOCH$_3$, AlOCOCF$_3$, SiCl$_2$ or Si(OH)$_2$, and wherein in formula I'', both Y groups are hydrogen ion or lithium ion, and at least four of the radicals $R^1$ to $R^{16}$ in each of formulas I' and I'' are each independently of the others a nitrogen-containing heterocyclic radical which is monosubstituted or polysubstituted by $C_1$–$C_4$-alkyl, benzyl, phenylethyl or phenyl and is bonded to the phthalocyanine structure via a ring nitrogen atom of the heterocyclic radical which is a member selected from the group consisting ofpyrrolidinyl, pyrazolidinyl, imidazolidinyl, oxazolidinyl, isoxazolidinyl, piperidinyl, piperazinyl, morpholinyl and thiomorpholinyl, and any remaining radicals $R^1$ and $R^{16}$ are each hydrogen, halogen, hydroxysulfonyl of $C_1$–$C_4$-dialkylsulfamoyl.

8. The phthalocyanine as claimed in claim 1, wherein formula I" conforms to the formula Ia or Ib;

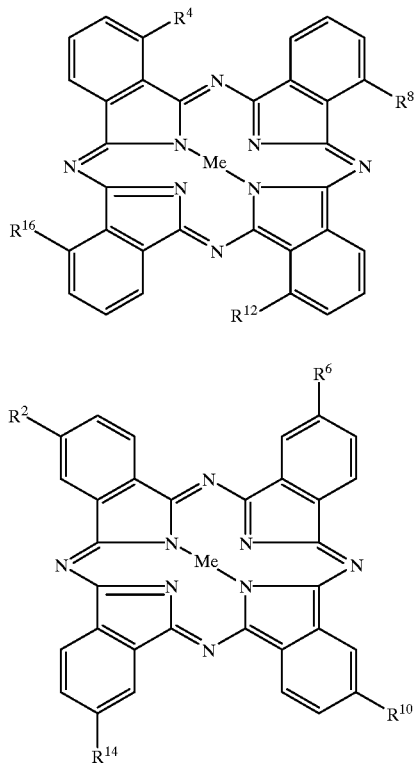

where the radicals $R^4$, $R^8$, $R^{12}$ and $R^{16}$ and $R^2$, $R^6$, $R^{10}$ and $R^{14}$ are each a heterocyclic radical and Me is in each case as defined above, and their positional isomers in relation to the radicals $R^4$, $R^8$, $R^{12}$ and $R^{16}$ and also $R^2$, $R^6$, $R^{10}$ and $R^{14}$.

9. A method of marking a liquid, comprising:
mixing the phthalocyanine of claim 1 into the liquid to be marked.

10. The method according to claim 9, wherein said liquid is a mineral oil.

11. A mineral oil comprising at least one phthalocyanine as claimed in claim 1.

* * * * *